United States Patent [19]

Philippe

[11] Patent Number: 5,626,855
[45] Date of Patent: May 6, 1997

[54] SERINE COMPOUNDS, THEIR PREPARATION AND THEIR USE IN COSMETIC OR DERMATOLOGICAL COMPOSITIONS

[75] Inventor: Michel Philippe, Wissous, France

[73] Assignee: L'Oreal, Paris, France

[21] Appl. No.: 437,809

[22] Filed: May 9, 1995

[30] Foreign Application Priority Data

May 9, 1994 [FR] France ................... 94 05689

[51] Int. Cl.$^6$ ............... A61K 7/00; A61K 7/06
[52] U.S. Cl. ............ 424/401; 424/70.1; 514/844; 560/155
[58] Field of Search ............ 424/401, 70.1; 514/844; 560/155

[56] References Cited

U.S. PATENT DOCUMENTS

| | | | |
|---|---|---|---|
| 5,230,890 | 7/1993 | Philippe et al. | 424/401 |
| 5,230,980 | 7/1993 | Maniar | 430/137 |
| 5,354,510 | 10/1994 | Vanlerberghe et al. | 252/548 |
| 5,368,857 | 11/1994 | Corcoran et al. | 424/401 |
| 5,431,904 | 7/1995 | Laney | 424/65 |

FOREIGN PATENT DOCUMENTS

| | | |
|---|---|---|
| 0408448 | 1/1991 | European Pat. Off. |
| 0577506 | 1/1994 | European Pat. Off. |
| WO86/03746 | 7/1986 | WIPO |

*Primary Examiner*—Amy Hulina
*Attorney, Agent, or Firm*—Finnegan, Henderson, Farabow, Garrett & Dunner, L.L.P.

[57] ABSTRACT

At least one serine compound corresponding to the Formula I:

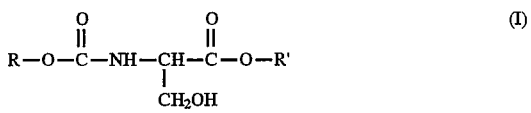

in which R and R', which are identical or different, represent a linear or branched hydrocarbon radical having from 8 to 30 carbon atoms, or the D-optical isomer of Formula I, the L-optical isomer of Formula I, or a non-racemic mixture of at least two of the optical isomers; the preparation of these compounds and their use, especially in cosmetic or pharmaceutical compositions intended for treating or caring for the hair or for the skin.

5 Claims, No Drawings

SERINE COMPOUNDS, THEIR PREPARATION AND THEIR USE IN COSMETIC OR DERMATOLOGICAL COMPOSITIONS

The subject of the invention is new serine derivatives and their preparation. Another subject of the invention is cosmetic or dermatological compositions containing these new derivatives.

Serine is an amino acid which is important for the hair and for the skin because it is a precursor of ceramides, which are compounds of the stratum corneum of the epidermis and of the hair and are considered essential by their barrier properties which prevent, for example, problems of water permeability.

Known serine derivatives, as exemplified in Patent Application EP-A-0,408,448, the disclosure of which is hereby incorporated by reference, include lipoamino acids containing a urethane functional group. These are ionic compounds with a single chain which form part of cosmetic or dermatological compositions for skin treatment and which give excellent results on dry skins.

The inventor has found new serine compounds which have at least the same properties for the skin as those described in Patent Application EP-A-0,408,448 but which additionally are of great advantage in hair treatment as a disentangling or smoothing agent.

The subject of the invention is therefore serine compounds or derivatives which correspond to the formula:

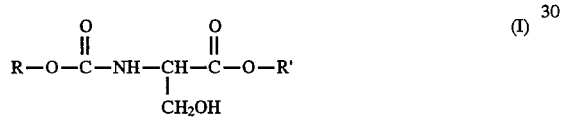

wherein R and R', which are identical or different, represent a linear or branched hydrocarbon radical having from 8 to 30 carbon atoms. The invention is drawn to at least one racemic mixture of a serine compound of formula (I), the D-optical isomer of formula (I), the L-optical isomer of formula (I), or a non-racemic mixture of at least two of the optical isomers.

Hydrocarbon radical is understood to mean any saturated or unsaturated hydrocarbon radical having from 8 to 30 carbon atoms.

According to a preferential embodiment of the invention, R and R', which are identical or different, are saturated radicals or radicals which contain a double bond.

According to another embodiment of the invention, R and R', which are identical or different, preferably contain from 8 to 18 carbon atoms.

Mention may be made, as compounds of formula (I), of:
dodecyl 3-hydroxy-2-[N-(hexadecyloxycarbonyl)amino] propionate,
octyl 3-hydroxy-2-[N-(hexadecyloxycarbonyl)amino] propionate,
hexadecyl 3-hydroxy-2-[N-(hexadecyloxycarbonyl)amino] propionate,
dodecyl 3-hydroxy-2-[N-(2-ethylhexyloxycarbonyl)amino] propionate,
octyl 3-hydroxy-2-[N-(2-ethylhexyloxycarbonyl)amino] propionate,
hexadecyl 3-hydroxy-2-[N-(2-ethylhexyloxycarbonyl) amino]propionate,
dodecyl 3-hydroxy-2-[N-(dodecyloxycarbonyl)amino] propionate,
octyl 3-hydroxy-2-[N-(dodecyloxycarbonyl)amino] propionate,
hexadecyl 3-hydroxy-2-[N-(dodecyloxycarbonyl)amino] propionate,
dodecyl 3-hydroxy-2-[N-(oleyloxycarbonyl)amino] propionate,
octyl 3-hydroxy-2-[N-(oleyloxycarbonyl)amino]propionate,
hexadecyl 3-hydroxy-2-[N-(oleyloxycarbonyl)amino] propionate.

The following are particularly preferred among the above compounds:
dodecyl 3-hydroxy-2-[N-(hexadecyloxycarbonyl)amino] propionate,
octyl 3-hydroxy-2-[N-(hexadecyloxycarbonyl)amino] propionate, and
hexadecyl 3-hydroxy-2-[N-(hexadecyloxycarbonyl)amino] propionate.

The present invention is also drawn to a process for the preparation of the compounds of formula (I) as defined above. According to this process, an N-liposerine salt corresponding to the formula:

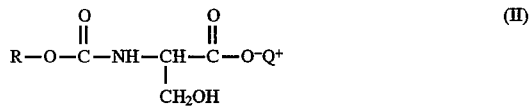

and an activated hydrocarbon derivative corresponding to the formula:

in which R and R', which are identical or different, represent a linear or branched hydrocarbon radical having from 8 to 30 carbon atoms;

$Q^+$ is an organic or inorganic cation;

and X an activating group, are reacted in the presence of a phase transfer agent.

According to a preferential embodiment of the invention, R and R' which are identical or different, are saturated radicals or radicals which contain a double bond.

According to another embodiment of the invention, R and R', which are identical or different, preferably contain from 8 to 18 carbon atoms.

Mention may be made, as $Q^+$ cation example, of alkali metal cations such as potassium.

The X activating group can be a halogen atom or a mesyloxy, brosyloxy or tosyloxy radical.

It is possible to use, as phase transfer agent, any compound commonly used in this type of reaction. A solid/liquid phase transfer agent is preferentially used. A quaternary ammonium derivative, such as, for example, trioctylmethylammonium chloride, is preferably used.

The liposerine salts used in this process are, for example, the salts of the compounds cited in Patent Application EP-A-0,408,448, such as the salts of N-(hexadecyloxycarbonyl)serine, N-(2-ethylhexyloxycarbonyl)serine or N-(dodecyloxycarbonyl) serine. These can also be the salts of N-(oleyloxycarbonyl) serine.

The liposerine salts used can be provided in the form of their D or L isomers or of a mixture of these forms. In other words, beginning with either a D- or L-optical isomer of formula (II), the respective D- or L-optical isomer of formula (I) can be obtained. Alternatively, a racemic mixture of formula (II) can be used to prepare a racemic mixture of formula (I) followed by conventional separation of the mixture into the respective D- or L-optical isomers.

According to a first embodiment of the process of the invention, (A), the phase transfer reaction generally takes place at a temperature above 20° C., preferably from 60° C. to 180° C. and more preferably from 80° C. to 120° C. The duration of the reaction is then generally greater than 2 hours, preferably from 2 to 15 hours and more preferably from 4 to 10 hours.

According to a second embodiment of the process according to the invention, (B), the phase transfer reaction can take place by subjecting the reaction mixture, in the chamber of a microwave oven, to a nominal power generally greater than 100 watts for a reaction time generally of 1 to 15 minutes and preferably from 2 to 7 minutes.

Whatever the method of preparation used, (A or B), the molar ratio of the compound of formula (III) to the compound of formula (II) is generally from 1 to 5, and preferably from 1.2 to 2.

The phase transfer agent is, in the reaction mixture, whatever the procedure used, in a proportion of generally from 0.1% to 10 %, and preferably from 0.5 % to 5 %, by weight with respect to the weight of compound of formula (I).

Once the reaction is complete, the salts can be removed by washing with water. The ester thus obtained is then purified and characterized according to techniques known to those skilled in the art.

The present invention is further drawn to cosmetic or dermatological compositions containing at least one racemic mixture of a serine compound, the D-optical isomer, the L-optical isomer, or the non-racemic mixture corresponding to the formula (I).

In the compositions according to the invention, the compounds of formula (I) are generally present at a concentration which can range from 0.05 % to 20 %, and preferably from 0.5 % to 10 %, by weight with respect to the total weight of the composition.

These compositions contain the ingredients commonly used in cosmetics for this type of preparation. This, they can contain at least one additive chosen from fatty alcohols, thickeners, fatty acid esters, esters of fatty acids and glycerol, silicones (volatile or nonvolatile, functionalized or nonfunctionalized), surface-active agents, fragrances, preservatives, sunscreens, proteins, vitamins, polymers, organic or inorganic oils and any other additive conventionally used in the cosmetics field.

The compositions of the invention can also be provided in any, optionally vesicular, solution or dispersion form of the derivatives as defined above.

All these compositions are prepared according to the usual methods known to those skilled in the art.

A fourth subject of the invention relates to the use of a composition as defined above in treating and/or caring for the hair or for the skin.

A fifth subject of the invention relates to a process for cosmetic treatment, in which a composition as defined above is used, intended especially for improving smoothing and/or disentangling of hair.

A sixth subject of the invention relates to a process for cosmetic or dermatological treatment, in which a composition as defined above is used, intended for treating the skin.

Examples of the preparation of serine compounds or derivatives corresponding to the formula (I), as well as examples of compositions containing them, will now be given, by way of illustration. These examples should in no way limit the scope of the invention.

EXAMPLE 1

Preparation of dodecyl 3-hydroxy-2-[N-(hexadecyloxycarbonyl)amino]propionate:

The experimental method referenced B in the text was used for this preparation.

The following were introduced into a 30 ml crystallized dish:

4.86 mmol (2 g) of potassium 3-hydroxy-2-[N-(hexadecyloxycarbonyl)amino]propionate, 9.72 mmol (2.32 ml) of bromododecane, 0.04 g of trioctylmethylammonium chloride.

The mixture was irradiated for 3 minutes in a microwave oven (Menu Masters 3100i, 2450 MHz, nominal power 1400 watts).

After cooling, a beige wax was obtained which was dissolved at approximately 40° C. in 8 ml of methanol per gram of wax. An insoluble white material (potassium bromide) remained and was removed by filtering off.

The filtrates were cooled to 4° C. A white precipitate appeared which was collected by filtering off and then dried.

The weight obtained was 1.8 g for 2.63 g expected, i.e. a yield of 68%.

White-coloured crystals were obtained, the characteristics of which were:

Melting point (obtained by Mettler FP 89): M.p.=65° C. (solvent=methanol)

Elemental analysis: $C_{32}H_{63}NO_5 \cdot 1.5H_2O$, M.W.=569

| | C | H | N |
|---|---|---|---|
| Calculated | 67.56 | 11.69 | 2.46 |
| Theory (+1.5 $H_2O$) | 67.88 | 10.97 | 2.37 |

$^{13}C$ NMR: conformed to the expected structure.

EXAMPLE 2

Preparation of octyl 3-hydroxy-2-[N-(hexadecyloxycarbonyl)amino]propionate.

The preparation was carried out as in Example 1, according to Process B, by mixing:

4.86 mmol (2 g) of potassium 3-hydroxy-2-[N-(hexadecyloxycarbonyl)amino]propionate, 9.72 mmol (1.68 ml) of bromooctane, 0.04 g of trioctylmethylammonium chloride.

An amber liquid was obtained, which congealed on cooling, which was dissolved at approximately 40° C. in 7 ml of methanol per gram of product. A white insoluble material (potassium bromide) remained and was removed by filtering off.

The filtrates were cooled to 4° C. A white precipitate appeared which was collected by filtering off and then dried.

The weight obtained was 1.2 g for 2.36 g expected, i.e. a yield of 50 %.

The characteristics of the product were:

Melting point-(obtained by Mettler FP 89): M.p.=55° C. (solvent=methanol)

Elemental analysis: $C_{28}H_{55}NO_5 \cdot 1.5H_2O$, M.W.=513

| | C | H | N |
|---|---|---|---|
| Calculated | 65.59 | 11.4 | 2.73 |
| Theory (+1.5 $H_2O$) | 65.50 | 10.77 | 2.92 |

$^{13}C$ NMR: conformed to the expected structure.

EXAMPLE 3

Preparation of hexadecyl 3-hydroxy-2-[N-(hexadecyloxycarbonyl)amino]propionate

This product was obtained according to Process A.

The following were introduced into a 500 ml round-bottomed flask equipped with a stirrer, a thermometer and a vertical reflux condenser:

27 mmol (10 g) of 3-hydroxy-2-[N-(hexadecyloxycarbonyl)amino]propanoic acid, 27 mmol (3 g) of potassium tert-butoxide, 100 ml of dimethylformamide.

The reaction mixture was maintained at 20° C. with stirring for 1 hour.

The following were then added:

200 ml of N-methylpyrrolidone.

27 mmol of hexadecyl bromide (8.2 g).

The reaction mixture was heated at 80° C. for 2 ½ hours.

The solvents were removed under reduced pressure.

The residue obtained was taken up in 120 ml of ethyl acetate and 120 ml of water.

Two phases and a precipitate were obtained. The precipitate was collected by filtering off and taken up in a mixture of ethyl acetate and heptane to which aqueous ammonia had been added.

Two phases and a precipitate were obtained. The precipitate was filtered off and then dried. The weight of this precipitate was 6.8 g.

This product was then purified on a column of silica gel.

The weight of pure product obtained was 4.1 g, corresponding to a yield of 22.8%.

The characteristics of this product were:

Melting point (obtained by Mettler FP 89): M.p.=70° C. (solvent=acetone)

Elemental analysis: $C_{36}H_{71}NO_5$, M.W.=598

|  | C | H | N |
|---|---|---|---|
| Calculated | 72.31 | 11.97 | 2.34 |
| Theory | 72.87 | 11.96 | 2.36 |

$^{13}C$ NMR: conformed to the expected structure.

EXAMPLE 4

Preparation of hexadecyl 3-hydroxy-2-[N-(hexadecyloxycarbonyl)amino]propionate

The preparation was carried out as in Example 1, according to Process B, by mixing:

230 mmol (95 g) of potassium 3-hydroxy-2-[N-(hexadecyloxycarbonyl)amino]propionate, 230 mmol (69.9 g) of bromohexadecane, 1.9 g of trioctylmethylammonium chloride.

Irradiation lasted 4 minutes.

An amber liquid was obtained which congealed on cooling.

The solid obtained was finely divided, coarsened in water and filtered off and then taken up in acetone, filtered off and dried.

85 g of product were thus obtained from the 137.5 g expected, i.e., a yield of 61.8 %, the characteristics of which were:

Melting point (obtained by Mettler FP 89): M.p.=70° C. (solvent=acetone)

Elemental analysis: $C_{36}H_{71}NO_5$, M.W.=598

|  | C | H | N |
|---|---|---|---|
| Calculated | 72.31 | 11.97 | 2.34 |
| Theory | 72.98 | 12.05 | 2.36 |

$^{13}C$ NMR: conformed to the expected structure.

EXAMPLE 5

A comparative test was carried out on the effects of smoothing the hair of a cosmetic composition according to the invention, containing 1% hexadecyl 3-hydroxy-2-[N (hexadecyloxycarbonyl)amino]propionate in isopropanol, with respect to a control consisting of isopropanol.

This test determined the coefficient of friction of hair by measuring the force applied to a control mass in order to make it slide at a constant rate over two hairs held tight in the same way. Measurement was carried out by making the mass slide from the root towards the end of the hair (R→E) and vice versa (E→R).

| Hair | Treatment | Coefficient of friction | |
|---|---|---|---|
|  |  | R → E | E → R |
| Natural | Control | 0.101 ± 0.003 | 0.127 ± 0.004 |
|  | Composition according to the invention | 0.084 ± 0.003 | 0.116 ± 0.006 |

Application of the composition according to the invention resulted in a marked decrease in the coefficient of friction, in particular in the root→end (R→E) direction, thus demonstrating an improvement in the smoothing or disentangling of the hair.

EXAMPLE 6

A conditioner having the following composition was prepared:

| | |
|---|---|
| hexadecyl 3-hydroxy-2-[N-(hexadecyloxycarbonyl)amino]propionate | 0.2 g |
| Behenyltrimethylammonium chloride (at 80% in a 15/85 water/isopropanol mixture sold under the name of DC 80 by the Company Toho) | 2 g |
| Water | q.s. for 100 g |
| The solution was adjusted to a pH of 7.4. | |

After the various ingredients were mixed, a fluid milky solution was obtained. This solution was applied to hair after a shampoo for a few minutes and was then rinsed with water. Hair which can be more easily styled was thus obtained.

EXAMPLE 7

A treating cream having the following composition was prepared:

| | |
|---|---|
| Ceteareth-30 (according to the CTFA nomenclature). | 2.5 g* |
| Hydroxyethyl cellulose | 0.5 g |
| Behenyltrimethylammonium chloride (at 80% in a 15/85 water/isopropanol mixture sold | 1.5 g |

-continued

| | |
|---|---|
| under the name of DL 80 by the Company Toho) | |
| Hexadecyl 3-hydroxy-2-[N-(hexadecyloxy-carbonyl)amino]propionate | 0.5 g |
| Water | q.s. for 100 g |
| The solution was adjusted to pH 6. | |

After mixing, a white-coloured cream was obtained which was easily applied to hair and made it easy to disentangle.

EXAMPLE 8

The following cream shampoo was prepared:

| | |
|---|---|
| Sodium lauryl ether sulphate, oxyethylenated with 2.2 mol | 8 g* |
| Coco-betaine (according to the CTFA nomenclature) | 4 g* |
| Glycol distearate | 1 g |
| Cocoyl diethanolamide | 1 g |
| Hexadecyl 3-hydroxy-2-[N-(hexadecyloxy-carbonyl)amino]propionate | 0.2 g |
| Preservative, dye, fragrance and water: | q.s. for 100 g |

*: expressed as weight of active material in Examples 7 and 8.

After mixing, an iridescent cream shampoo was obtained which was comfortable on application, which had a gentle lather and which resulted in ease of disentangling and a smoothing effect to hair.

What is claimed is:

1. A cosmetic or dermatological composition, comprising at least one racemic mixture of a serine compound corresponding to Formula I;

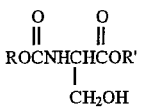

wherein R and R', which are identical or different, are selected from a linear or branched hydrocarbon radical having from 8 to 30 carbon atoms;
the D-optical isomer of Formula (I);
the L-optical isomer of Formula (I); or
a non-racemic mixture of at least two of said optical isomers, in a cosmetically acceptable carrier.

2. The cosmetic or dermatological composition according to claim 1, wherein said composition contains by weight with respect to the total weight of the composition from 0.05% to 20% of the at least one racemic mixture of a serine compound, the D-optical isomer, the L-optical isomer, or the non-racemic mixture.

3. A cosmetic or dermatological composition according to claim 2, wherein said composition contains by weight with respect to the total weight of the composition from 0.5% to 10% of said at least one racemic mixture of a serine compound, the D-optical isomer, the L-optical isomer, or the non-racemic mixture.

4. A method of treating or caring for the hair, comprising the step of applying to the hair a cosmetic composition according to claim 1.

5. A method of treating or caring for the skin, comprising the step of applying to the skin a cosmetic or dermatological composition according to claim 1.

* * * * *